United States Patent
Lee et al.

(10) Patent No.: US 11,718,744 B2
(45) Date of Patent: Aug. 8, 2023

(54) PHOTO-CURABLE RESIN COMPOSITIONS CONTAINING IMPACT MODIFIER FOR THREE DIMENSIONAL PRINTING AND CURED DENTAL PRODUCT MADE OF THE SAME

(71) Applicant: DENTCA, Inc., Torrance, CA (US)

(72) Inventors: Jason Lee, Torrance, CA (US); Shuang Xiao, Torrance, CA (US); Jun Kyu Park, Torrance, CA (US)

(73) Assignee: DENTCA, Inc., Torrance, CA (US)

( * ) Notice: Subject to any disclaimer, the term of this patent is extended or adjusted under 35 U.S.C. 154(b) by 126 days.

(21) Appl. No.: 17/214,603

(22) Filed: Mar. 26, 2021

(65) Prior Publication Data

US 2022/0306856 A1  Sep. 29, 2022

(51) Int. Cl.
| | |
|---|---|
| C08L 33/14 | (2006.01) |
| A61K 6/60 | (2020.01) |
| A61K 6/62 | (2020.01) |
| A61K 6/887 | (2020.01) |

(52) U.S. Cl.
CPC .................................... *C08L 33/14* (2013.01)

(58) Field of Classification Search
CPC .. A61K 6/60; A61K 6/62; A61K 6/887; C08L 33/14
USPC .......................................................... 522/96
See application file for complete search history.

(56) References Cited

U.S. PATENT DOCUMENTS

| | | | |
|---|---|---|---|
| 5,496,682 A | 3/1996 | Quadir et al. | |
| 6,263,351 B1 * | 7/2001 | Wolfe | G06F 16/93 715/236 |
| 6,362,251 B1 * | 3/2002 | Alkemper | A61K 6/30 106/35 |
| 6,680,152 B2 * | 1/2004 | Ishii | G03F 7/027 430/18 |
| 6,881,360 B2 * | 4/2005 | Stange | A61C 13/0003 264/494 |
| 7,476,347 B1 | 1/2009 | Sun et al. | |
| 7,927,538 B2 | 4/2011 | Moszner et al. | |
| 8,822,570 B2 * | 9/2014 | Yoshioka | C09D 7/68 523/201 |
| 10,420,712 B2 * | 9/2019 | Ruppert | A61K 6/16 |
| 10,519,319 B2 | 12/2019 | Lin et al. | |
| 11,174,338 B2 * | 11/2021 | Liska | C08G 18/44 |
| 2002/0045149 A1 * | 4/2002 | Alkemper | A61K 6/54 433/212.1 |
| 2009/0192240 A1 * | 7/2009 | Benz | A61K 6/893 523/116 |
| 2011/0049738 A1 | 3/2011 | Sun et al. | |
| 2012/0208000 A1 * | 8/2012 | Yoshioka | C09D 4/06 524/533 |
| 2013/0324635 A1 * | 12/2013 | Shimizu | A61K 6/887 525/185 |
| 2014/0131908 A1 * | 5/2014 | Sun | A61C 13/0013 264/16 |
| 2015/0231041 A1 * | 8/2015 | Bublewitz | A61K 6/76 522/152 |
| 2016/0324730 A1 | 11/2016 | Lee | |
| 2017/0156990 A1 * | 6/2017 | Ruppert | A61F 2/30942 |

FOREIGN PATENT DOCUMENTS

| | | |
|---|---|---|
| EP | 2118169 | 11/2009 |
| EP | 3135270 | 3/2017 |

OTHER PUBLICATIONS

PCT International Application No. PCT/US2022/071395, Written Opinion of the International Searching Authority dated Jun. 15, 2022, 11 pages.

* cited by examiner

*Primary Examiner* — Sanza L. McClendon

(74) *Attorney, Agent, or Firm* — Lee, Hong, Degerman, Kang & Waimey PC

(57) ABSTRACT

A photocurable composition includes: about 45 to about 55 weight % of aromatic urethane di(meth)acrylate monomer having two urethane linkages and two acryloyloxy groups; about 20 to about 30 weight % of monofunctional (meth) acrylate monomer having acryloyl groups; about 8 to about 18 weight % of bifunctional (meth)acrylate monomer having ethoxy groups; about 5 to about 15 weight % of impact modifier having core-shell structure; about 0.2 to about 5.0 weight % of at least one kind of ultraviolet/visible (UV/Vis) light-photo-polymerization initiator; and at least one colorant.

6 Claims, No Drawings

PHOTO-CURABLE RESIN COMPOSITIONS CONTAINING IMPACT MODIFIER FOR THREE DIMENSIONAL PRINTING AND CURED DENTAL PRODUCT MADE OF THE SAME

FIELD OF INVENTION

The present disclosure relates to liquid type photo-curable resin compositions and a method for producing dental products by a three-dimensional printing process using the compositions containing impact modifier. In particular, the present disclosure relates to dental compositions having sufficient hardness and toughness for dental products. Such compositions are used in three-dimensional printing to manufacture dentures having a distinctive denture base.

DESCRIPTION OF THE RELATED ART

In recent years, three-dimensional printing technologies have been used to produce a large number of items in a short period of time. There are several ways to build three-dimensional articles using photo-curable materials.

One of the most efficient methods for three-dimensional printing is a stereolithography (SLA) method. In the stereolithography method, the photo-curable material, which is in a liquid form, is layered on a vat or spread on a sheet, and a predetermined area of the layered material is exposed to the ultraviolet (UV)/visible (Vis) light that is controlled by a digital micro-mirror device or is controlled by a liquid crystal panel. In the stereolithography method, additional layers are repeatedly or continuously laid and each layer is cured until a desired three-dimensional article is formed.

The stereolithography method is further subdivided into two categories. One is to use the line laser of UV/Vis light to bring the chemical reaction on the photo-curable material and solidify the cured material. The other method is to use the two-dimensional exposure of UV/Vis light to cure the material. Generally, the first method is known as stereolithography (SLA) and the second method is known as digital light processing (DLP).

Another technology for three-dimensional printing is an inkjet printing method of which the photo-curable material and support material are simultaneously jetted or only the photo-curable material is jetted through a single nozzle or a series of tiny nozzles onto a building plate and the applied material is then cured by ultraviolet/visible (UV/Vis) light. This method is also referred to as a layer-by-layer jetting method.

Currently, either DLP or SLA type of printing method is more popular than the inkjet type printing system due to its relatively simpler machine with lower printer price and open system for various materials.

In the dental field, most of dental products, such as crown, bridge, splint, mouthguards, nightguards, and dentures, are customized to fit for an individual person, and thus, it is difficult to produce them by a mass production method. The conventional processes to make customized dental products are labor intensive and time-consuming. However, utilizing the 3D printing technology, the customized dental devices with the accuracy of several microns can be produced effectively.

In general, conventional dental compositions or mixtures react slowly and have high viscosity. For example, (meth) acrylate materials, such as methyl methacrylate, and high molecular weight poly methyl methacrylate have been used as materials for manufacturing artificial teeth and denture base resin because they are inexpensive and have good transparency, excellent moldability, and good physical properties. The methyl methacrylate monomer has characteristic odor and is relatively volatile while high molecular weight polymethyl methacrylate has high viscosity and stickiness. Therefore, the conventional dental compositions are not suitable for 3D printing.

However, there have been attempts to produce dental products using three-dimensional printing technologies. For example, U.S. Pat. Nos. 5,496,682 and 7,927,538 disclose light-curable slips for stereolithographic preparation of dental ceramics. According to these patent documents, a flowable mixture, including sinterable inorganic particles, a photo-curable monomer, a photo-initiator and a dispersant, is spread over a substrate and cured in a selective pattern. Subsequent layers of the mixture are applied over the substrate and cured to build a three-dimensional body. Photo-curable materials used in systems disclosed in these patent documents play roles only as a binder to hold a certain form until the printed shape is solidified by a sintering process.

Nevertheless, since a main component of the mixture is sinterable inorganic particles, a sintering process is required to remove organic binder. In addition, the method disclosed in these patent documents provides only ceramic artificial teeth which may be easily broken by impact.

Further, U.S. Pat. No. 7,476,347 and U.S. Pat. Application Pub. No. 2011/0049738 disclose a process for making dentures having integral teeth and a denture base by inkjet type three-dimensional printing. In these patent documents, the cured specimen in a mold showed excellent mechanical properties.

However, in these patent documents, wax-like polymerizable materials were used in the printer, and since the wax-like polymerizable materials without filler are not readily available, they need to be custom-synthesized, incurring additional time and costs. Moreover, according to some embodiments disclosed in these patent documents, materials mixed with more than 70% filler required 10 minutes to cure in a mold due to their slow reaction rate and high viscosity. Furthermore, there was difficulty in using the composition mixed with filler having different particle sizes for jetting in three-dimensional printing.

U.S. Pat. No. 10,519,319 B2 discloses methods and materials for making dental products by three-dimensional printing. In this patent document, the materials are composed of 20-80 wt % ethoxylated bisphenol A dimethacrylate, 0 to 75 wt % of diurethane dimethacrylate; 0 to 10 wt % triethylene glycol dimethacrylate; and 0.01 to 10 wt % photo-initiator.

Certain dental products such as splint, nightguard, and dentures are required to have appropriate strength and toughness. These strength and toughness properties in conventional dental products can be achieved by optimizing the mixture of polymethylmethacrylate (PMMA) of thermoplastic polymer and methylmethacrylate monomer. However, availability of the photo-curable materials using 3D printing method for dental products is limited due to the limited raw materials to obtain the appropriate strength and toughness.

Material strength value of the dental products such as bending strength which is expressed as flexural strength and flexural modulus is good index of material usage. For example, mouthguards are used to reduce damage to teeth and to prevent the noise associated with bruxing or grinding. If strength and stiffness of the material used in the dental product are too high, it will bring discomfort when the user wears it and it may be broken easily. However, if the material used in the dental product is soft and tough, comfortableness will increase and it will be less prone to breaking because the material will be easily deformed by the force due to lowered strength and stiffness. Therefore, it is difficult to maintain both the strength and toughness in the material used in the dental product.

SUMMARY

Photo-curable liquid compositions used for dental products and a method for making dentures using the compositions and three-dimensional printing technology are provided. The inventive compositions for manufacturing dental prosthesis have suitable viscosity and curing rate for three-dimensional printing, providing appropriate bending performance and toughness properties desired for denture base. The inventive compositions also allow effective operation time for manufacturing dental prosthesis.

According to one exemplary embodiment, a composition includes: about 45 to about 55 weight % of aromatic urethane di(meth)acrylate monomer having two urethane linkages and two acryloyloxy groups (I); about 20 to about 30 weight % of monofunctional (meth)acrylate monomer having acryloyl groups (II); about 8 to about 18% weight % of difunctional (meth)acylate monomer having ethoxy groups (III); about 5 to about 15 weight % of impact modifier having core-shell structure (IV); about 0.2 to about 5.0 weight % of at least one kind of ultraviolet/visible (UV/Vis) light-photo-polymerization initiator; and at least one colorant.

The aromatic urethane di(metha)acrylate monomer having two urethane linkages and two acryloyloxy groups is a compound represented by the following formula (1):

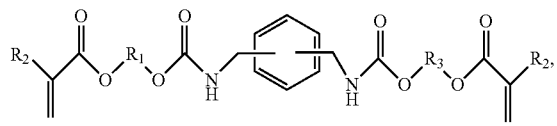

Formula (1)

wherein $R_1$ is divalent linear or branched alkane groups that may independently have substituents, and $R_2$ is independent methyl groups or hydrogen atoms. In one aspect of formula (1), $R_1$ is a divalent chain hydrocarbon groups having 2 to 8 carbon atoms and do not have a substituent, and $R_2$ independently represents a hydrogen atom or a methyl group. In formula (1), the two substitutions on aromatic ring can be either ortho, meta or para positions.

The monofunctional (meth)acrylate monomer having acryloyl groups contains at least one of a compound represented by the following formula (2):

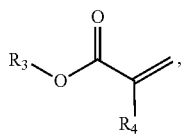

Formula (2)

wherein $R_3$ is a monovalent functional group having 6 to 20 carbon atoms and having an aromatic or alicyclic structure. The aromatic structure may be benzylic groups with various substitutes and the alicyclic structure may be cycloalkyl groups with various substitutes. In formula (2), $R_4$ independently represents a hydrogen atom or a methyl group.

The difunctional (meth)acylate monomer having ethoxy groups has at least one of ethoxy groups as a middle block and the (meth)acrylate groups at both ends, and is represented by the following formula (3):

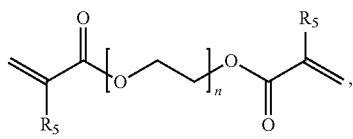

Formula (3)

wherein $R_5$ independently represents a hydrogen atom or a methyl group, n is repeat of ethoxy groups, and n is one of integers 1 to 6.

In one aspect, the impact modifier is a core-shell polymer with a rubbery core such as a copolymer containing a diolefin, an inner graft stage comprised mainly of a hard polymer such as a polymer containing a vinyl aromatic monomer, an intermediate sealer stage comprised mainly of an alkyl acrylate monomer, and an outer shell comprised mainly of alkyl methacrylate monomer to provide compatibility of the core-shell polymer with the matrix.

The core-shell type impact modifier into the acrylate resin formulation provides the excellent dispersibility in a liquid state mixture and after curing, and excellent effect of improving toughness without affecting the hardness of the composition.

The embodiment disclosed herein provides a photocurable composition which is used for the production by stereolithography of a dental prosthesis, a medical device for intraoral use, and which has sufficient toughness and excellent flexural strength and modulus after being subjected to post-curing.

The cured products obtained by curing the photocurable composition which contains impact modifier provide total fracture work of 500-1100 J/m2 and flexural strength of 50-100 MPa.

DETAILED DESCRIPTION

The present disclosure relates to photocurable compositions used to produce the toughened dental prosthesis using a three-dimensional printing system. The photo-curable compositions according to the present disclosure includes; about 45 to about 55 weight % of aromatic urethane di(meth) acrylate monomer having two urethane linkages and two acryloyloxy groups (I); about 20 to about 30 weight % of monofunctional (meth)acrylate monomer having acryloyl groups (II); about 8 to about 18 weight % of bifunctional (meth)acylate monomer having ethoxy groups (III); about 5 to about 15 weight % of impact modifier having core-shell structure (IV); about 0.2 to about 5.0 weight % of at least one kind of ultraviolet/visible (UV/Vis) light-photo-polymerization initiator; and at least one colorant.

It has been found that the combination of components (I) to (IV) identified above results in a photocurable composition possessing a suitable viscosity and allowing fast laser curing for 3D printing based on the SLA or DLP technology. The composition disclosed herein yields three-dimensional articles having an excellent fracture toughness and sufficient bending strength and modulus after post-curing, thus being suitable as a material for manufacturing of a dental prosthesis.

The composition disclosed herein has a flexural strength in the range of 50-100 MPa and flexural modulus in the range of 1500-2500 MPa, and total fracture work of 500-1100 J/m$^2$ in photocurable product obtained by post-curing. Most of photocurable composition after the post-curing does satisfy either the flexural strength and flexural modulus or fracture toughness because of the ambitendency properties between flexural properties and fracture toughness.

In general, flexural strength and flexural modulus usually represent hardness of materials and fracture toughness is related with flexible and soft properties. Hence if the flexural strength and flexural modulus of the composition reveals high value, the fracture toughness value may be low. Maintaining the sufficient flexural properties and fracture toughness on the photocurable composition, specifically 3D printable resin composition, has been studied.

In a dental use, the minimum 50 MPa of flexural strength and 1500 MPa of flexural modulus at human body temperature on the cured product of the photocurable composition are required because it provides sufficient hardness for its purpose. The maximum 100 MPa of flexural strength and 2500 MPa of flexural modulus on the cured product of the photocurable composition provide adequate hardness without causing the pain when used in oral cavity.

The flexural strength of the cured product obtained by curing the photocurable composition disclosed herein is preferably 50 MPa to 100 MPa, and particularly preferably 65 MPa to 90 MPa. For example, the range of suitable flexural strength is from 65 MPa to 90 MPa. Further, the total fracture work of the cured product obtained by curing the photocurable composition disclosed herein is preferably 500 J/m$^2$ or more. Within this range, a better usability and strength can be obtained. All fracture work of the cured product is preferably at least 500 J/m$^2$, more preferably at least 600 J/m$^2$. The upper limit of the total fracture work does not need to be specified, but is preferably less than 1200 J/m$^2$, for example.

By setting the above range, when it is formed into a medical device to be used in the oral cavity such as a denture, good feeling of use can be obtained without causing pain and it can be easily removed after wearing. Further, since the flexural strength is 100 MPa or less and the total fracture work is 500 J/m$^2$ or more, it is easy to put on and take off when it is used as a medical device in the oral cavity, and the putting on and taking off is repeated which is related with durability.

In accordance with ISO 20795-2, the flexural strength requires 50 MPa or more and the flexural modulus requires 1500 MPa or more at 37° C. to be used in dental orthodontic purpose. Therefore, the cured product of the photocurable composition disclosed herein can be used as orthodontic appliances in the oral cavity if suitable feeling of use, strength and durability can be achieved.

By keeping the total fracture work high while suppressing the flexural strength, it is possible to make orthodontic appliances with excellent usability and strength. Further, by setting the flexural strength and the total fracture work within the above ranges, it is easy to put on and take off when used as orthodontic appliances in oral cavity, and orthodontic appliances having excellent durability when repeatedly putting on and taking off can be obtained.

The photocurable composition disclosed herein is suitable to print out the dental products using a stereolithography. The stereolithography is one of three-dimensional printing methods by exposing certain portion of the photocurable mixture to the ultraviolet laser of light. The photocurable composition disclosed herein is particularly suitable for SLA or DLP type stereolithography.

In recent years, a large number of three-dimensional printing technologies have been introduced and are available to produce three-dimensional objects. For example, three-dimensional printing technologies include selective laser sintering (SLS), fused deposition molding (FDM), laminate object manufacturing (LOM), three-dimensional inkjet printing, and stereolithography. These three-dimensional printing technologies find use in a variety of fields, for example, jewelry, footwear, architecture, engineering and construction, automotive, aerospace, dental and medical industries, education, geographic information systems, civil engineering, and many others.

Among these technologies, three-dimensional printing methods using stereolithography technology is most effectively optimized for speed, low cost, high resolution, and ease-of-use, making them suitable for visualizing during conceptual stages of engineering design and early-stage functional testing. A 3D printer using the stereolithography technology is used to obtain a three-dimensional structure by irradiating a photocurable composition with a spot-shaped (SLA type) or two-dimensional (DLP) ultraviolet laser light.

The photocurable composition disclosed herein is stored in a container and the spot-shaped or two-dimensional shaped laser light is irradiated to the photocurable mixture through the transparent bottom of the container in order to form a certain shape of layer having a desired thickness on the building plate. The desired thickness is maintained by a pre-set gap between the building plate and the container. Once a layer is cured by UV/Vs light, a building plate moves away from the container according to the printer setting parameter and the fresh material fills the gap between the container and building plate. After filling with the fresh material, the building plate moves down to the container by a pre-set gap and the fresh material is exposed on the spot-shaped or two-dimensional shaped laser light again to create a certain shape of layer.

This process is repeated until all layers are formed. According to this printing method, since only one material is loaded in the container and its container can be heated up to a certain degree such as 30° C. in some SLA or DLP type printer, the viscosity of photocurable composition is less restricted compared to the inkjet type 3D printer. For the inkjet type 3D printer, the material should go through a tiny nozzle, and thus, the viscosity of material is strongly restricted.

The 3D printable and photocurable composition disclosed herein has a viscosity of 500 mPa·s to 6000 mPa·s at 25° C. and is suitable for producing dental products by stereolithography technology. The viscosity of the composition is determined using a single cylinder type rotational viscometer method with 100 rpm at 25° C. in accordance with ISO 2555: 2018. The lower limit of the viscosity is preferably 500 mPa·s, more preferably 1000 mPa·s. The upper limit of the viscosity is preferably 6000 mPa·s, more preferably 5000 mPa·s. When the composition is too viscous, 3D printing by the stereolithography technology causes the printing failure and its printing time will take longer than the low viscous composition.

The inventive compositions for manufacturing dental prosthesis using 3D printer have suitable viscosity and curing rate, providing appropriate bending performance and toughness properties desired for denture base. The inventive compositions also allow effective operation time for manufacturing dental prosthesis.

According to one exemplary embodiment, a composition includes: about 45 to about 55 weight % of aromatic urethane di(meth)acrylate monomer having two urethane linkages and two acryloyloxy groups (I); about 20 to about 30 weight % of monofunctional (meth)acrylate monomer having acryloyl groups (II); about 8 to about 18 weight % of bifunctional (meth)acrylate monomer having ethoxy groups (III); about 5 to about 15 weight % of impact modifier having core-shell structure (IV); about 0.2 to about 5.0 weight % of at least one kind of ultraviolet/visible (UV/Vis) light-photo-polymerization initiator; and at least one colorant.

The aromatic urethane di(meth)acrylate monomer having two urethane linkages and two acryloyloxy groups is a compound represented by the following formula (1):

Formula (1)

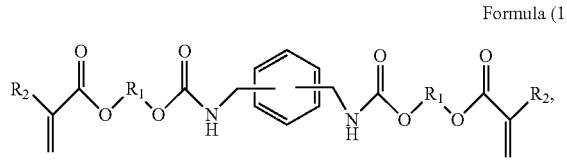

wherein $R_1$ is divalent linear or branched alkane groups that may independently have substituents, and $R_2$ is independent methyl groups or hydrogen atoms. In formula (1), $R_1$ is a divalent hydrocarbon groups having 2 to 8 carbon atoms and do not have a substituent, and $R_2$ independently represents a hydrogen atom or a methyl group. Two substitutions on aromatic ring can be either ortho, meta or para positions as shown by the following formula:

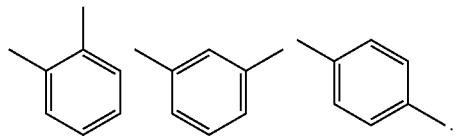

In formula (1), $R_1$ is divalent linear or branched alkane groups which may independently have a substituent. The liner or branched alkane groups have preferably 2 to 10 carbon atoms, more preferably 2 to 6 carbon atoms. The substituent may have an hydrogen atom; an alkyl group having 1 to 4 carbon atoms such as methyl group, ethyl group, propyl group, butyl group, or the like; an alkoxy group having 1 to 4 carbon atoms such as a methoxy group, an ethoxy group, a propyoxy group, a butoxy group, or the like; a cycloalkyl group having 3 to 6 carbon atoms such as a cyclopropyl group, cyclobutyl, cyclopentyl, cyclohexyl, or the like; and alkoxyphenyl groups such as a methoxyphenyl group, an ethoxyphenyl group, a propoxyphenyl group, or the like.

In formula (1), the urethane linkage as shown below is formed by the reaction between hydroxyl group and isocyanate group.

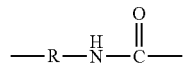

Urethane di(meth)acrylate monomer may be prepared in a known manner from the hydroxyl acrylate monomer and isocyanate monomer. It requires two molecules of mono hydroxyl terminated acrylate monomer and diisocyanate terminated monomers. Preferred mono-hydroxyl terminated acrylate monomer suitable for synthesizing urethane linkage are presented as follows:

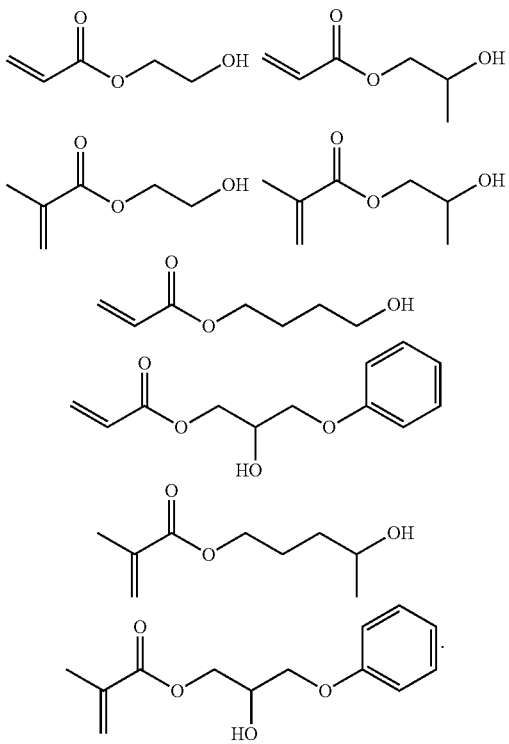

Preferred diisocyanate monomers for synthesizing urethane linkage are presented as follows:

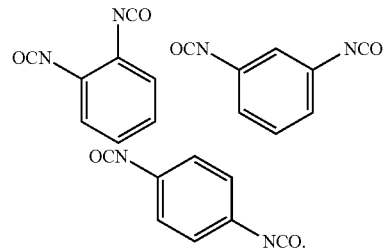

In one example embodiment, the monofunctional (meth) acrylate monomer having acryloyl groups can be employed as component (II) in the composition and is represented by the following general formula (2):

Formula (2)

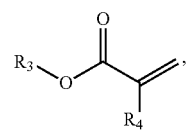

wherein $R_3$ is a monovalent functional group having 6 to 20 carbon atoms or having an alicyclic or benzylic structure. Examples of the monovalent functional group having 6 to 20 carbon atoms include an arylene group, an alkylene arylene group, an alkylene arylene alkylene group, an arylene alkyene arylene group, a cycloalkyl groups, and benzyl groups. In formula (2), $R_4$ independently represents a hydrogen atom or a methyl group.

Preferably, formula (2) with $R_3$ having from 6 to 20 carbon atoms may have a structure represented by the following structures:

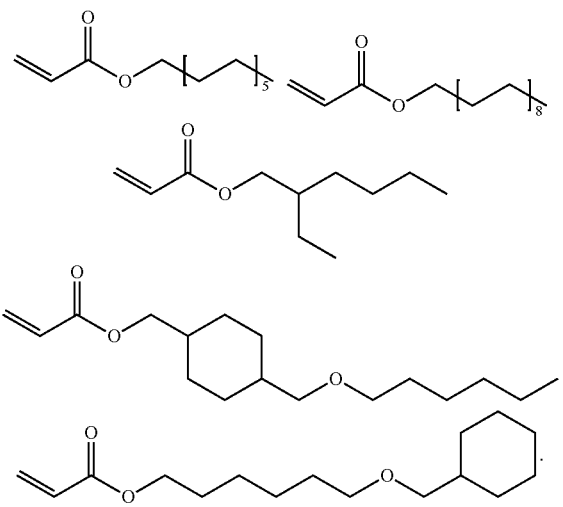

Furthermore, in formula (2), $R_3$ having an alicyclic or benzylic structure can be presented by the following structures:

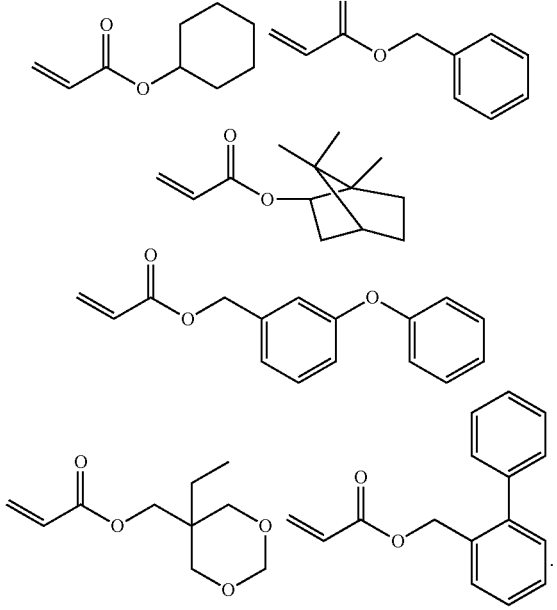

In one example embodiment, the bifunctional (meth) acrylate monomer having ethoxy groups has at least one of ethoxy groups as a middle block and the (meth)acrylate groups at both ends represented by the following formula (3):

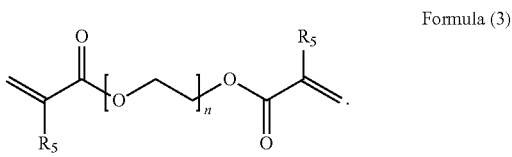

Formula (3)

In formula (3), $R_5$ independently represents a hydrogen atom or a methyl group, n is the repeat of ethoxy groups, and n may be any one of integers 1 to 6.

Preferably, the number of ethoxy groups in formula (3) is 1, 2, or 3. Its structure is represented by the following structures:

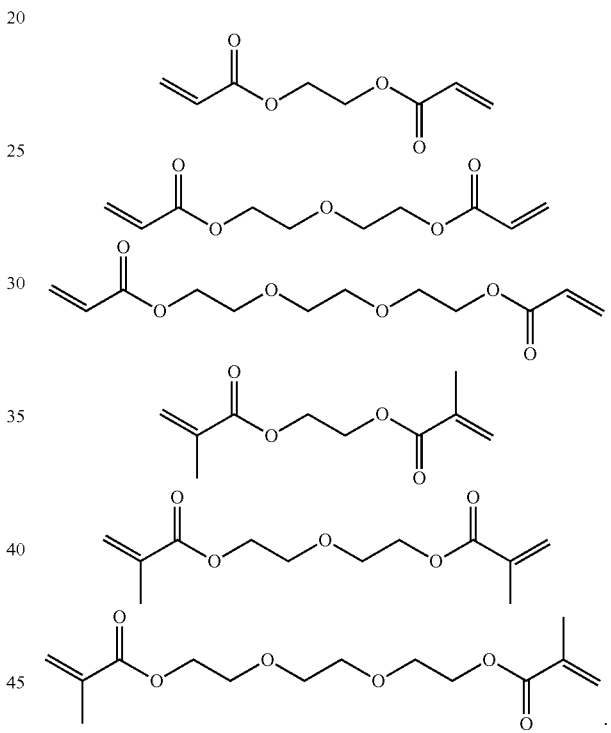

Impact modifiers have been mixed into various thermoplastic resins or curable mixtures as an additive to reinforce the toughness of the final resins. There are various types of impact modifiers such as reactive liquid rubber or nitrile rubber in the curable mixture, but the reactive liquid rubber is subjected to phase separation at the time of curing and the physical properties of cured product are deteriorated by the change of morphologies of the cured products.

To prevent such problems, core-shell type of impact modifier may be used in the curable resin formulation. The core-shell type of impact modifier is a multilayer-structure polymer particle. The modifier usually has a rubber core having low glass transition such as diolefin or butyl acrylate and methyl methacrylate shell. Some impact modifier may have the intermediate layer made of polystyrene. The core with low glass transition provides the impact resistance and toughness at low temperature and the shell provides the compatibility and the coupling with matrix resin to be effective for toughing the cured products.

Preferably, the core-shell type of impact modifier is composed of 65-85 parts of diolefin core with the glass transition temperature lower than −80° C., 8 to 14 parts of the intermediate layer made of vinyl aromatic monomer to provide the sealing effect, and 8 to 20 parts of the shell composed of alkyl methacrylate monomer. Furthermore, the particle size of core shell type of impact modifier composed of three layers is less than 200 μm.

Illustrative examples of free-radical photo-initiators include, but are not limited to, acetophenone, anisoin, antraquinone, (benzene) tricarbonylchromium, benzil, benzoin, benzoin ethyl ether, benzoin isobutyl either, benzoin methyl ether, benzophenone, 3,3',4,4'-benzophenonetetracarboxylic dianhydride, 4-benzoylbiphenyl, 2-benzyl-2-(dimethylamino)-4'-morpholinobutyrophenone, 4,4'-bis(diethylamino)benzophenone, 4,4'-bis(dimethylamino)benzophenone, camphorquinone, 2-chlorothioxanthen-9-one, (cumene)cyclopentadienyliron(II)hexafluorophosphate, dibenzosuberenone, 2,2-diethoxyacetophenone, 4,4'-dihydroxybenzophenone, 2,2-dimethoxy-2-phenylacetophenone, 4-(dimethylamino)benzophenone, 4,4'-dimethylbenzil, 2,5-dimethylbenzophenone, 3,4-dimethylbenzophenone, 4'-ethoxyacetophenone, 2-ethylanthraquinone, ferrocene, 3'-hydroxyacetophenone, 4'-hydroxyacetophenone, 3-hydroxybenzophenone, 4-hydroxybenzophenone, 1-hydroxycyclohexyl phenyl ketone, 2-hydroxy-2-methylpropiophenone, 2-methylbenzophenone, 3-methylbenzophenone, methylbenzoylformate, 2-methyl-4'-(methylthio)-2-morpholinopropio-phenone, phenanthrenequinone, 4'-phenoxyacetophenone, thioxanthen-9-one, triacrylsulfonium hexafluoroantimonate salts, and triarylsulfonium hexafluorophophate salts.

Among the previously identified free-radical photo-initiators, the acylphosphine oxide compounds provide excellent polymerizability in UV/Vis light and have been recently used in the dental field. The composition using a visible light photo-initiator composed of the acylphosphine oxide compound showed an excellent curability of a thin-layer surface, which is an important property for the three-dimensional printing. Therefore, a visible light photo-initiator used for artificial teeth and denture base may be (bis)acylphosphine oxides or preferably camphorquinone.

Among (bis)acylphosphine oxides used as a photo-initiator, examples of the acylphosphine oxides include 2,4,6-trimethylbenzoyldiphenylphosphine oxide, 2,6-dimethyoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate. Examples of the bisacylphosphine oxides include bis-(2,6-dichlorobenzoyl)phenylphosphine oxide, bis-(2,6-dichlorobenzoyl)-2,5-dimethylphenylphosphine oxide, bis-(2,6-dichlorobenzoyl)-4-prophylphenylphosphine oxide, bis-(2,6-dichlorobenzoyl)-1-naphthylphosphine oxide, bis-(2,6-dimethoxylbenzoyl)-2,4,4-trimethylpentylphosphine oxide, bis-(2,6-dimethoxybenzoyl)-2,5-dimethylphenylphosphine oxide, bis-(2,4,6-trimethylbenzoyl)phenylphosphine oxide, and (2,5,6-trimethylbenzoyl)-2,4,4-trimethylpentylphosphine oxide.

The cationic photo-initiators may be onium salts. The cationic species of the photo-initiator may be, for example, iodonium, sulfonium, oxoisothiochromanium, or similar compounds. These compounds are known and commercially available.

In one example embodiment, the mixture optionally may include a pigment composition including a pigment or combination of pigments to provide a desired color. Various combinations of pigments and dyes may be used. In another example embodiment, the amount of the combination of pigments may be less than about 0.5 weight %, preferably less than about 0.3 weight % based on the total weight of the composition.

The pigments should be dispersed in the formulation without separating and settling down from the compositions for the shelf life of the composition. The viscosity of the composition with pigments may be affected by the size of the pigments. A preferred size of the pigment is from about 0.1 to about 600 nm, more preferably from about 10 to about 200 nm.

The color of the pigments is not limited to a particular color. Possible colors of the pigments include, for example, white, yellow, orange, black, green, red, violet, and like.

In one example embodiment, the composition may optionally include a surface tension reducing agent to provide lower surface tension by lowering surface energy, better wettability, and a small drop size to the formulation to minimize the satellite drops tail during the jetting or printing process. Examples of the surface tension reducing agent include silicone surface additives, marketed by Byk Chemie under the trade name Byk or marketed by Dow Corning under the trade name Dow Corning series.

In one example embodiment, the composition may also include one or more stabilizers optionally. Suitable stabilizers include, but are not limited to, 4-methoxyphenol, butylated hyrdorxytoluene (2,6-di-t-butyl-4-methylphenol), phenothiazine, bistridecylthiodipropionate, and hinder amines.

EXAMPLES

Example 1

First of all, 53.7 parts of aromatic urethane diacrylate which has formula (1) structure was diluted with 18.8 parts of monofunctional acrylate monomer which has formula (2) because the aromatic urethane diacrylate is too viscous in the reactor. When the mixture was diluted with a static mixer, the additional 6.2 parts of monofunctional acrylate monomer and 13.9 parts of bifunctional acrylate monomer were added into the mixture. When all three components are fully mixed, 1.8 parts of powder type photo-initiator was added to the mixture and stirred. Once the photo-initiator was fully dissolved in the mixture, the liquid mixture was transparent. In this condition, the 5.6 parts of core-shell type of impact modifier composed of methylmethacrylate butadiene styrene copolymer was added into the mixture and stirred for 2-3 days at room temperature to achieve homogenous mixture.

Examples 2 to 7

The same procedure as in example 1 was carried out except the composition ratio are different among the examples. In this manner, each of the photo polymerizable resin mixtures for manufacturing of three-dimensional articles by a digital light processing method was prepared by mixing relevant components shown in Table 1 to obtain a homogenous system.

TABLE 1

| Component | 1 | 2 | 3 | 4 | 5 | 6 | 7 |
|---|---|---|---|---|---|---|---|
| Aromatic urethane diacrylate | 53.7 | 49.6 | 50.9 | 54.6 | 48.7 | 51.8 | 52.7 |
| Monofunctional (meth)acrylate monomer | 25.0 | 23.1 | 23.6 | 21.3 | 22.7 | 28.6 | 20.5 |
| Bifunctional (meth)acrylate monomer | 13.9 | 12.8 | 13.2 | 16.6 | 12.6 | 8.9 | 16.1 |
| Core-shell Impact modifier | 5.6 | 12.8 | 10.5 | 5.6 | 14.3 | 8.9 | 8.9 |
| Photo-initiator | 1.8 | 1.7 | 1.8 | 1.9 | 1.7 | 1.8 | 1.8 |

Example No./weight % of each component

Comparative Example 8

A similar composition using the same components without the impact modifier was prepared. Test specimens of the comparative example 8 for flexural strength and flexural modulus tests were printed according to ISO 20795-1:2013 and the post-curing process was performed. Post curing was carried out under UV/Vis curing equipment for 40 min.

Comparative Example 9

A same sample composition having the same ratio as Example 7 was prepared, except acrylic impact modifier was used instead of core-shell type of impact modifier which provided the compatibility with the matrix. Its composition is presented in Table 2. All three components were mixed together for two hours and then the photo-initiator was added to the mixture. Once the photo-initiator was fully dissolved in the mixture, the acrylic impact modifier was added and stirred for two days to make a homogenous mixture. The same physical properties using the same tools and method were measured and are presented in Table 4.

Comparative Example 10

A similar composition with a ratio using the same impact modifier but using different urethane acrylate, monofunctional acrylate, and bifunctional acrylate was prepared. The aliphatic urethane acrylate mixture (urethane acrylate with high urethane content (Trade Name N3D-F230 from Sartomer) and urethane dimethacrylate (Trade name CN1964 from Sartomer) was used. The monofunctional acrylate monomer (Trade name N3D-M285 from Sartomer) with high Tg material was added as diluent. Epoxy acrylate monomer as a bifunctional acrylate monomer was used in Example 10. The reaction of the formulation was slow, the phenylbis(2,4,6-trimethylbenzoyl)-phoshineoxide as an effective photo-initiator was used in the formulation. Its composition is presented in Table 2. The same physical properties using the same tools and method were measured and are presented in Table 4.

TABLE 2

| Component | Example 8 (%) | Example 9 (%) | Example 10 (%) |
|---|---|---|---|
| Aromatic Urethane diacrylate | 71.1 | 52.7 | — |
| Aliphatic Urethane diacrylate | — | — | 58.3 |
| Monofunctional (meth)acrylate monomer | 12.2 | 20.5 | 13.9 |
| Bifunctional (meth)acrylate monomer | 14.7 | 16.1 | 20.4 |
| Impact Modifier | 0 | 8.9 | 5.6 |
| Photo-initiator | 2 | 1.8 | 1.8 |

Performance Evaluation Method

Test specimens of Examples 1-10 for flexural strength and flexural modulus, maximum intensity factor, and total facture work tests were printed according to ISO 20795-1:2013 using a 3D printer (cara 3D printer provided by Kulzer USA). After the printing, a post curing process on the test specimens was carried out under UV/Vis curing equipment for 40 min.

Specifically, the specimens for test of flexural strength and flexural modulus were obtained by printing (cara 3D printer provided by Kulzer USA) the test photocurable compositions to the size of 64 mm×10 mm×3.3 mm. The printed objects were irradiated with ultraviolet lights under the condition of 10 $J/m^2$. The cured objects were stored in the constant temperature water tank at 37±1° C. for 50±2 hours. After the conditioning, the flexural and flexural modulus were measured in accordance with ISO 20795-1:2013.

In addition, the total fracture work ($J/m^2$) was obtained by a fracture toughness test with a three-point bending test setup. The photocurable compositions of Examples 1-10 were printed by the 3D printer (cara 3D printer provided by Kulzer USA) to form the size of 39 mm×8 mm×4 mm objects and the printed objects were photocured by irradiating the printed objects with ultraviolet lights for 40 min. The obtained specimens were notched and stored in a constant temperature water bath at 37±1° C. for 7 days±2 hours in accordance with ISO 20795-1:2013. The fracture toughness test by three-point bending test was performed under the condition of 1.0±0.2 mm/min and the total fracture work ($J/m^2$) was measured.

The flexural strength and flexural modulus and toughness measurement were performed using the universal testing machine (Testresources—Model 140).

The viscosities of Examples 1-10 were determined using a single cylinder type rotational viscometer (Brookfield Viscometer—Model DV1) with 100 rpm at 25° C. in accordance with ISO 2555: 2018.

The results of physical properties measurement for Example 1-7 are presented in Table 3.

TABLE 3

| Physical Property | 1 | 2 | 3 | 4 | 5 | 6 | 7 |
|---|---|---|---|---|---|---|---|
| Viscosity (mPa · s) | 1604 | 4617 | 4289 | 1566 | 4825 | 3824 | 4128 |
| Flexural Strength (MPa) | 68.3 | 66.6 | 68 | 67.4 | 66.1 | 58.2 | 61.5 |

Example No.

TABLE 3-continued

| Physical Property | Example No. | | | | | | |
|---|---|---|---|---|---|---|---|
| | 1 | 2 | 3 | 4 | 5 | 6 | 7 |
| Flexural Modulus (MPa) | 2212.9 | 2149 | 2198.2 | 2104.7 | 2154.7 | 2009.1 | 1992.7 |
| Maximum Intensity Factor | 2.4 | 2.26 | 2.61 | 2.2 | 2.3 | 2.37 | 2.18 |
| Total Fracture Work (J/m$^2$) | 730.4 | 868.8 | 918.4 | 545.8 | 871.3 | 918.8 | 634.9 |

The results of physical properties measurement for comparative Examples 8-10 are presented in Table 4.

TABLE 4

| Physical Property | Example 8 | Example 9 | Example 10 |
|---|---|---|---|
| Viscosity (mPa · s) | 1156 | 3021 | 4308 |
| Flexural Strength (MPa) | 82 | 52.5 | 45 |
| Flexural Modulus (MPa) | 2520.7 | 1598.6 | 1288.9 |
| Maximum Intensity Factor | 1.99 | 1.7 | 2.34 |
| Total Fracture Work (J/m$^2$) | 321.5 | 433.7 | 926.9 |

It will be apparent to those skilled in the art that various modifications and variations can be made in the example embodiments of the present invention without departing from the spirit or scope of the invention. Thus, it is intended that the present invention covers the modifications and variations of the example embodiments disclosed herein provided they come within the scope of the appended claims and their equivalents.

What is claimed is:

1. A photocurable composition comprising:
   about 45 to about 55 weight % of aromatic urethane di(meth)acrylate monomer having two urethane linkages and two acryloyloxy groups;
   about 20 to about 30 weight % of monofunctional (meth) acrylate monomer having acryloyl groups;
   about 8 to about 18 weight % of bifunctional (meth) acrylate monomer having ethoxy groups;
   about 5 to about 15 weight % of impact modifier having core-shell structure;
   about 0.2 to about 5.0 weight % of at least one kind of ultraviolet/visible (UV/Vis) light-photo-polymerization initiator; and
   at least one colorant,
   wherein the aromatic urethane di(meth)acrylate monomer having two urethane linkages and two acryloyloxy groups is a compound represented by the following formula (1):

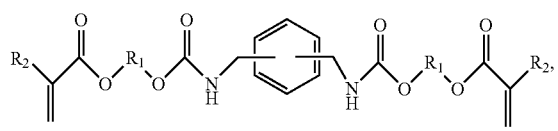

Formula (1)

wherein two substitutions on aromatic ring are either ortho, meta or para positions; $R_1$ is a divalent chain hydrocarbon groups having 2 to 8 carbon atoms and do not have a substituent; and $R_2$ independently represents a hydrogen atom or a methyl group.

2. The composition of claim 1, wherein the monofunctional (meth)acrylate monomer having acryloyl groups is represented by the following formula (2):

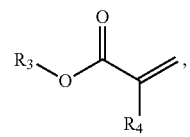

Formula (2)

wherein $R_3$ is a monovalent functional group having 6 to 20 carbon atoms and having an aromatic or alicyclic structure,
   wherein the aromatic structure comprises benzylic groups with various substitutes,
   wherein the alicyclic structure comprises cycloalkyl groups with various substitutes, and
   wherein $R_4$ independently represents a hydrogen atom or a methyl group.

3. The composition of claim 1, wherein the bifunctional (meth)acrylate monomer having ethoxy groups, having at least one of ethoxy groups as a middle block and (meth) acrylate groups at both ends, is represented by the following formula (3):

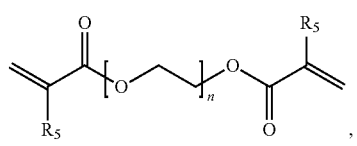

Formula (3)

wherein $R_5$ independently represents a hydrogen atom or a methyl group,
   wherein n is repeat of ethoxy groups, and
   wherein n is one of integers 1 to 6.

4. The composition of claim 1, wherein the core-shell structured impact modifier has 65 to 85 parts of a diolefin, 8 to 14 parts of an intermediate layer comprising a vinyl aromatic monomer, and 8 to 20 parts of outer shell comprising an alkyl methacrylate monomer.

5. The composition of claim 1, wherein the composition has a flexural strength of 50 to 100 MPa at 37° C. and total fracture work of 500-1100 J/m$^2$ at 25° C. after the composition is cured.

6. The composition of claim 1, wherein viscosity the composition is 1,000-5,000 cps at 25° C.

* * * * *